United States Patent [19]
Batts et al.

[11] Patent Number: 5,866,633
[45] Date of Patent: *Feb. 2, 1999

[54] MATERIAL AND METHOD FOR INHIBITING BACTERIAL GROWTH IN AN AQUEOUS MEDIUM

[75] Inventors: Gregory Nigel Batts, Bushey; Karen Leeming; Christoper Peter Moore, both of Harrow, all of United Kingdom

[73] Assignee: Eastman Kodak Company, Rochester, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 610,312

[22] Filed: Mar. 4, 1996

[30] Foreign Application Priority Data

Mar. 8, 1995 [GB] United Kingdom .................... 9504629

[51] Int. Cl.⁶ ........................................ C08K 5/45
[52] U.S. Cl. ............................. 523/122; 524/84; 524/606; 524/589; 524/590; 528/73; 424/409; 430/463; 422/28
[58] Field of Search ............................. 523/122; 524/84, 524/606, 589, 590; 528/73; 424/409; 430/463; 422/28

[56] References Cited

U.S. PATENT DOCUMENTS

| | | | |
|---|---|---|---|
| 2,870,015 | 1/1959 | Allen et al. ................................. | 96/109 |
| 4,552,591 | 11/1985 | Millar ..................................... | 106/18.33 |
| 4,640,948 | 2/1987 | Rasoul ..................................... | 524/606 |
| 4,996,261 | 2/1991 | Lebovits et al. ........................ | 523/177 |
| 5,104,649 | 4/1992 | Jansson et al. ........................ | 424/78.31 |
| 5,163,994 | 11/1992 | Klimesch et al. ........................... | 71/91 |
| 5,229,124 | 7/1993 | Rei et al. ................................. | 424/409 |
| 5,472,993 | 12/1995 | Kim et al. ................................. | 523/122 |
| 5,476,913 | 12/1995 | Kourai et al. ............................. | 526/310 |

FOREIGN PATENT DOCUMENTS

| | | |
|---|---|---|
| 0 095 907 | 7/1983 | European Pat. Off. . |
| 61-254506 | 11/1986 | European Pat. Off. . |
| 0 513 935 | 11/1992 | European Pat. Off. ........... C08J 3/22 |
| 601 674 | 6/1994 | European Pat. Off. . |
| 56-147702 | 11/1981 | Japan . |
| 848130 | 8/1960 | United Kingdom . |
| 1531431 | 11/1978 | United Kingdom ............. A01N 9/12 |
| 1587307 | 4/1981 | United Kingdom ............. C08F 8/42 |
| 2223662 | 4/1990 | United Kingdom ............. A01C 1/06 |

OTHER PUBLICATIONS

*Hawley's Condensed Chemical Dictionary,* New York, NY, Van Nostrand Reinhold, 1993, p. 132.

*Primary Examiner*—Andrew E. C. Merriam
*Attorney, Agent, or Firm*—John R. Everett

[57] ABSTRACT

A biocidal material comprises an organic biocide immobilized on a polymeric support characterized in that the support is water-insoluble and the biocide is covalently bound to the support by a hydrolytically stable covalent linkage. The material can be used for inhibiting bacterial growth in an aqueous medium e.g. the wash water of a photoprocessing system. The material can be housed in a flow-through container.

3 Claims, 3 Drawing Sheets

FIG. I

MATERIAL AND METHOD FOR INHIBITING BACTERIAL GROWTH IN AN AQUEOUS MEDIUM

FIELD OF THE INVENTION

The invention relates to a material, method and apparatus for inhibiting bacterial growth in an aqueous medium.

BACKGROUND OF THE INVENTION

Bacterial growth occurs in many systems in which aqueous media such as water, aqueous solutions and aqueous dispersions are employed.

For example, significant biofouling can occur in many areas of photoprocessing systems and, in particular, where low flow rate washes and water recycling is used. The problem may be overcome by adding biocides to the wash water tanks when bacterial biofilm formation becomes evident visually. However at this point the biocides are not particularly effective because the bacteria have attached to surfaces to form biofilms which have built up in layers. Hence, any biocide in solution can only reach the outer biofilm layer and not the inner layers of the biofilm. Furthermore, widespread use of such biocides is not desirable because they are relatively expensive and toxic chemicals which require specialised disposal to protect the environment.

Alternative methods of inhibiting bacterial growth in aqueous media involve the gradual release of a biocide through interaction with water e.g. by leaching.

GB-A-2 223 662 describes a coating composition for seeds which comprises an organic biocide chemically bound to a polymer by a hydrolytically unstable bond. The polymer gradually hydrolyses giving controlled release of the organic biocide.

Problem to be solved by the Invention

A problem associated with the prior art methods and materials for inhibiting bacterial growth in aqueous media is that biocide is released in the media.

Furthermore, there is a need for a method and materials in which the biocide is only used on demand when the bacteria are present.

Methods and materials which reduce the exposure of operators to toxic biocides are also sought.

SUMMARY OF THE INVENTION

The invention provides a biocidal material comprising an organic biocide immobilized on a polymeric support characterized in that the support is water-insoluble and the biocide is covalently bound to the support by a hydrolytically stable covalent linkage.

The invention also provides a method for inhibiting bacterial growth in an aqueous medium comprising contacting the aqueous medium with a biocidal material comprising an organic biocide immobilised on a polymeric support characterised in that the support is water-insoluble and the biocide is covalently bound to the support by a hydrolytically stable covalent linkage.

The invention also provides apparatus for inhibiting bacterial growth in an aqueous medium comprising a container having fluid inlet means and fluid outlet means said inlet and outlet means communicating with an inner chamber such that, when the apparatus is in use, fluid entering the inner chamber through the inlet means flows through the chamber and leaves the container through the outlet means characterised in that the inner chamber holds a biocidal material comprising a biocide immobilised on a support characterised in that the support is water-insoluble and the biocide is covalently bound to the support by a hydrolytically stable covalent linkage.

ADVANTAGEOUS EFFECT OF THE INVENTION

The invention removes the need for conventional dosing of biocides in solution, either directly or by gradual release, which has many drawbacks.

The biocide is only used on demand when the bacteria are present.

The biocide does not end up in the aqueous medium as it is consumed by the bacteria during their control.

The direct exposure of operators to toxic biocides is minimised.

DETAILED DESCRIPTION OF THE INVENTION

Figure 1:
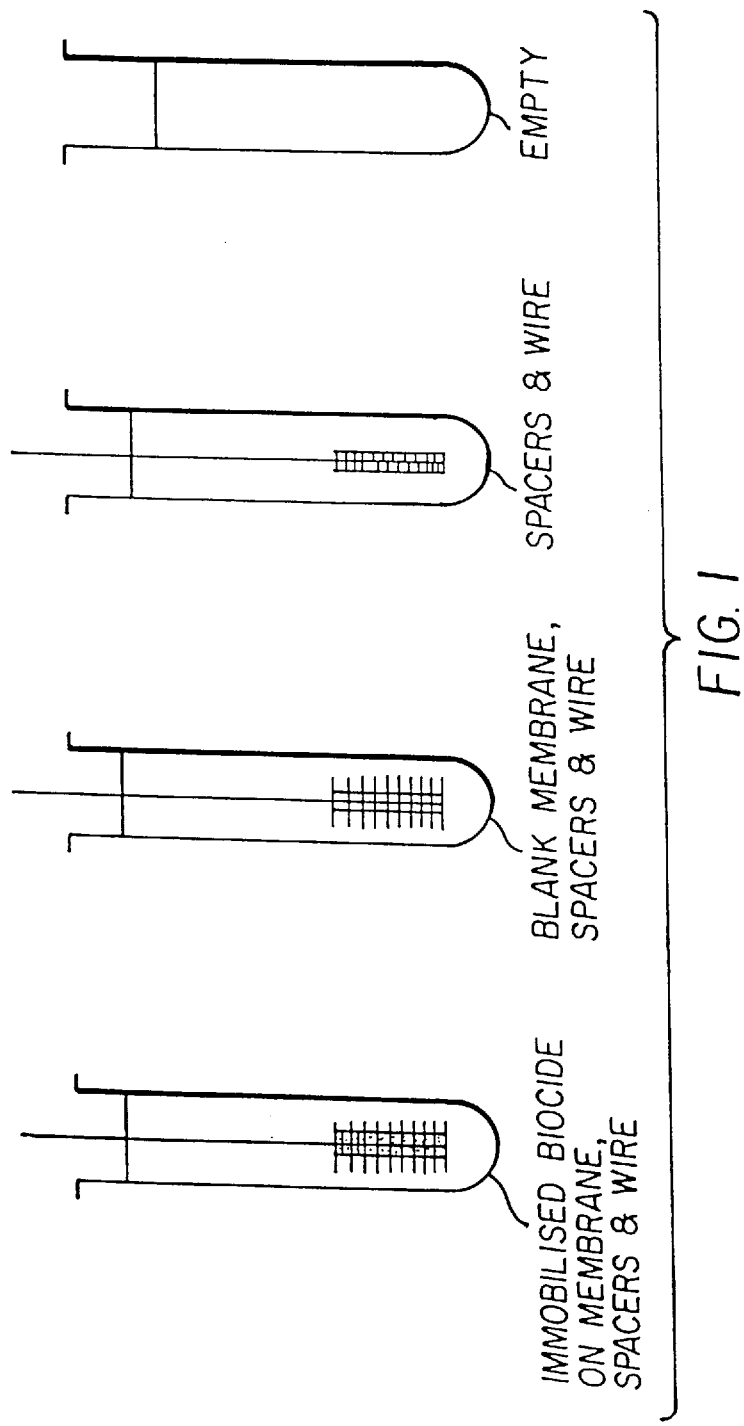
FIG. 1 is a schematic representation of apparatus used in evaluating the materials of the invention.

Biocides can be attached to a polymer support by covalent linkages that are variable in length and chemistry.

Suitable types of biocide include those described in "*Microbiocides for the Protection of Materials*", W. Paulus, published by Chapman Hall, 1993. They are agents capable of killing or inhibiting the multiplication of microorganisms such as bacteria, yeasts, fungi, algae and lichens. Examples include heterocyclic N,S compounds, compounds with activated halogen groups and quaternary ammonium salts.

Preferred biocides include those currently employed in the treatment of photoprocessing systems e.g. isothiazolinones.

Examples of isothiazolinone biocides are those having the structure

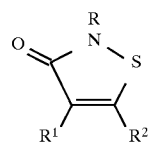

wherein

R represents hydrogen, alkyl, aryl, alkaryl and aralkyl; and, $R^1$ and $R^2$ independently represent hydrogen, halogen, alkyl, or $R^1$ and $R^2$ taken together represent the atoms necessary to complete a fused carbocyclic ring, e.g. a benzene ring.

Specific examples of commercially available isothiazolinone biocides include Proxel™ and Promexal™ (both manufactured by Zeneca) and Kathon™ (manufactured by Rohm and Haas). Promexal™ (manufactured by Zeneca):

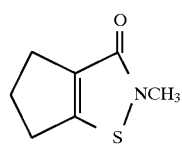

Kathon™ (manufactured by Rohm & Haas):

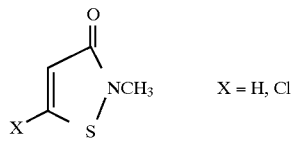

X = H, Cl

Polymers suitable for use as support materials include any inert, water-insoluble polymers.

Suitable types of polymer include condensation polymers such as polyurethanes, polyamides and polyureas; and polymers derived from one or more ethylenically unsaturated monomers such as polystyrene and polymethacrylates.

Preferably, the polymer comprises functional groups e.g. amide, urethane or ester groups which facilitate the covalent attachment of the biocide.

A number of different ways of covalently attaching molecules to polymers are known. In the resent invention, only those ways which result in a hydrolytically stable covalent linkage are suitable i.e. the biocide is not released from the polymer by hydrolysis. References teaching different attachment chemistries include J M Woodley, "*Solid Supports and Catalysts in Organic Synthesis*", Ellis Horwood, Chapter 9, 1992 and International Patent Application PCT/EP92/00129. A hydrolytically stable covalent linkage may comprise one or more alkylene groups interrrupted or terminated with one or more urethane, amide or ester groups.

In general terms, one or both of the biocide and polymer can be modified to react with the other. For example, a modified version of a known isothiazolinone biocide can be prepared in which the nitrogen atom bears a hydroxyalkyl group. The hydroxy group is available for reaction with a suitable functional group carried by the polymer. For example, a polyurethane can be modified by reaction with an alkylene diisocyanate to provide isocyanate groups pendant from the polymer backbone. Reaction of the modified isothiazolinone with the modified polyurethane results in the biocide being covalently attached to the polymer via a hydrolytically stable covalent linkage.

Polymer support materials can be provided in different forms e.g. sheets, fibres or particles. They may be porous or non-porous.

In use, the aqueous medium is brought into contact with the biocidal material. Different ways of achieving contact include passing the aqueous medium through a container e.g. a column containing the material in particulate form, passing the aqueous medium through a filter of the material and passing the aqueous medium over the material in the form of a surface coating.

The invention is of particular use in photoprocessing systems. Such systems comprise stages for developing, fixing, bleaching and washing an exposed photographic material. Each stage requires apparatus for applying the appropriate aqueous processing solution to the photographic material. The apparatus may comprise means for supplying, removing and, possibly, recirculating such solutions.

The method of the invention may be used to inhibit bacterial growth in the wash water or other solutions used in a photoprocessor.

Figure 3:
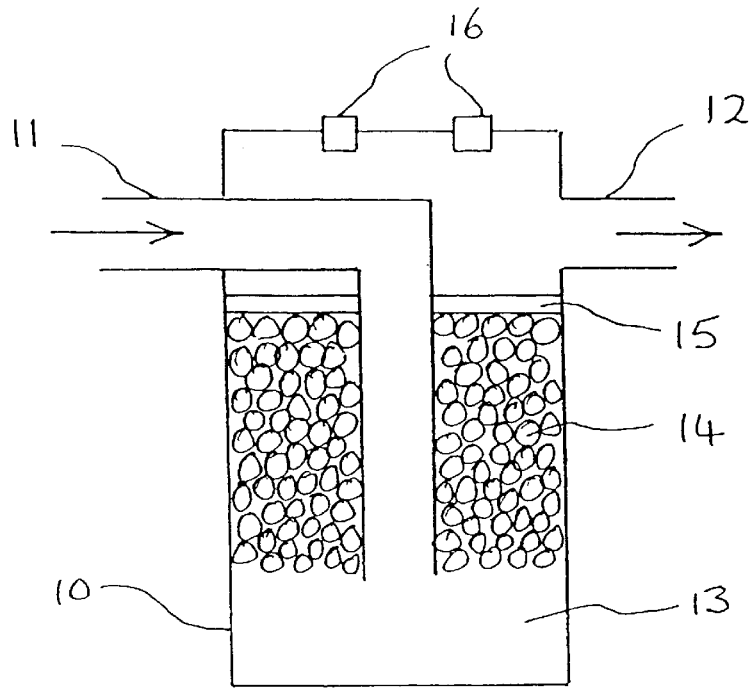
FIG. 3 is a schematic representation of apparatus for use in performing the method of the invention.

FIG. 3 is a schematic representation of apparatus for use in performing the method of the invention. The apparatus comprises a container 10 having fluid inlet means 11 and fluid outlet means 12 said inlet and outlet means 11, 12 communicating with an inner chamber 13 of the container. When the apparatus is in use, fluid entering the inner chamber through the inlet means 11 flows through the chamber 13 and leaves the container through the outlet means 12. The inner chamber 13 holds a biocidal material in accordance with the invention in the form of polymer beads 14. A filter 15 to retain the polymer beads is positioned at the top of the inner chamber to prevent loss of the beads from the device. The top of the container 10 is provided with plugs 16 for venting any gas which accumulates in the device.

Fluid entering the device flows down a central tube and subsequently flows up through the polymer beads. The arrows indicate the direction of the flow of fluid through the device.

Figure 4:
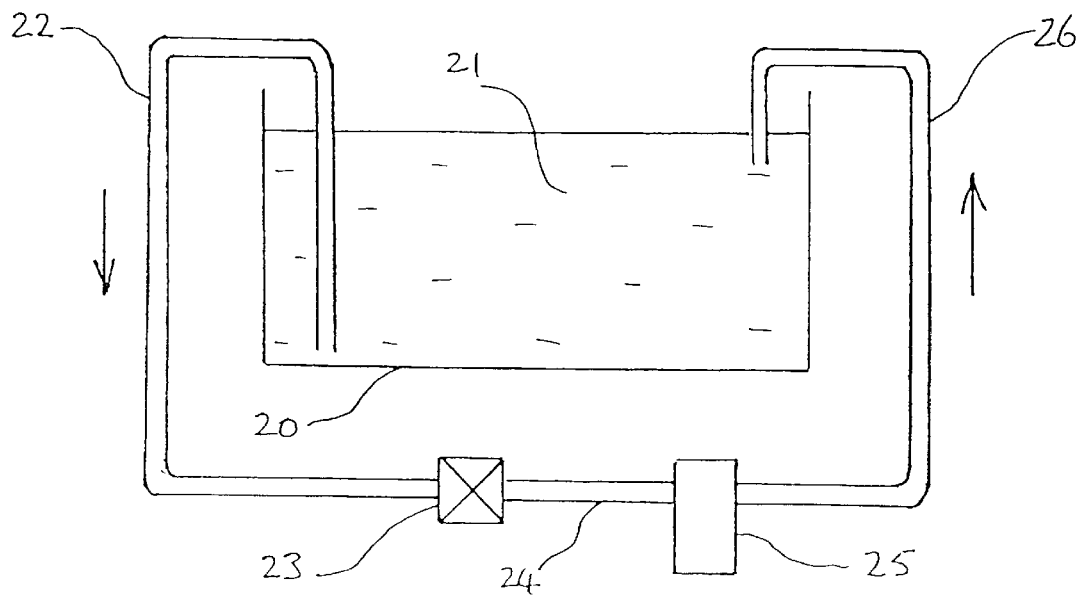
FIG. 4 is a schematic representation of the use of the apparatus shown in FIG. 4.

FIG. 4 is a schematic representation of the use of the apparatus shown in FIG. 3. A tank 20 containing water 21 is shown e.g. the wash water tank of a photoprocessor. Tubing 22 has an open end in the water 21 at the bottom of tank 20, the other end being connected to the inlet of a pump 23 outside the tank 20. Tubing 24 connects the outlet of the pump 23 to the inlet of a device 25 of the type shown in FIG. 4. One end of tubing 26 is connected to the outlet of device 25 and the other end opens into the top of tank 20.

In use, water is pumped from the bottom of tank 20 through device 25 and back into tank 20 in a recirculation loop. The arrows indicate the direction of the flow of water around the loop.

The invention is further illustrated by way of example as follows.

EXAMPLE 1

An analogue (1) of the commercially available biocide Proxel™ was prepared in three steps from commercially available starting materials as outlined in Scheme 1.

Scheme 1

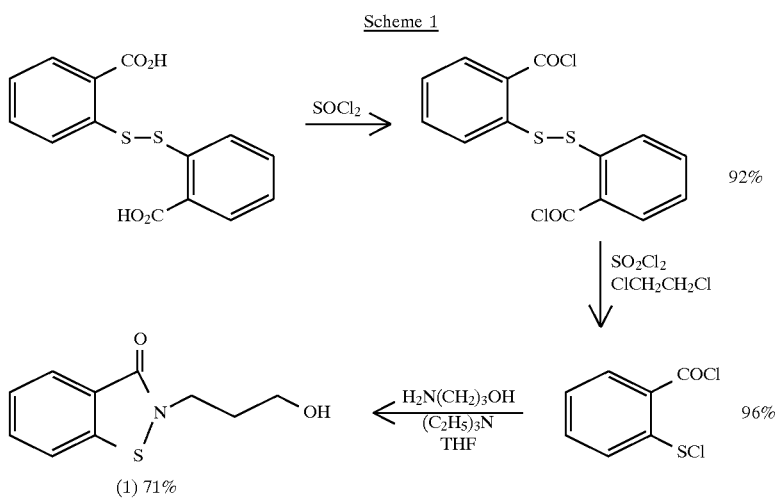

Subsequently it was attached covalently to a commercial polyurethane (Tecoflex™) by a two step heterogeneous process as outlined in Scheme 2.

Although the exact structure of the latter is unknown, it is believed to be related closely to Tecoflex™ and an identical

Scheme 2

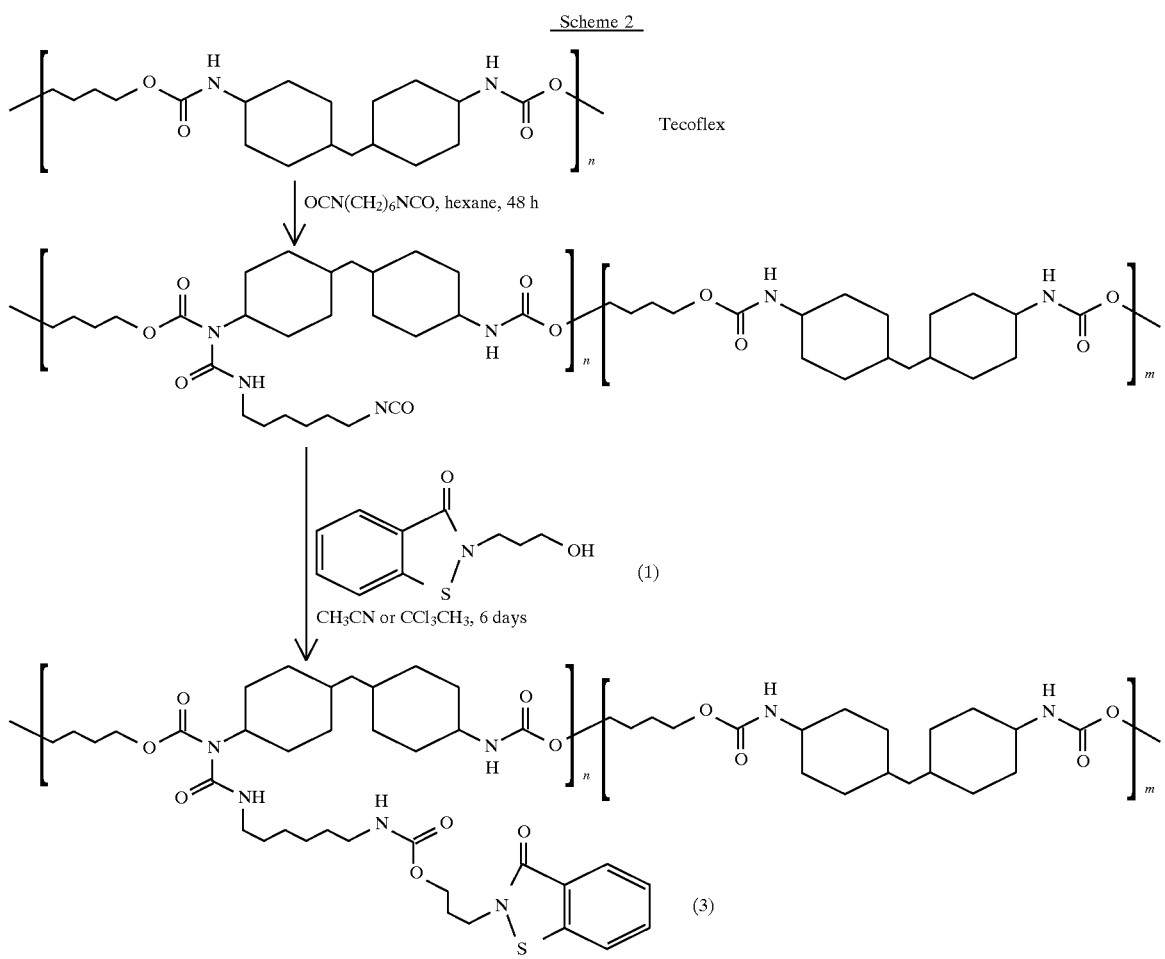

The polyurethane was supplied as an electrostatically spun fibre membrane. Further work was performed on another commercial polyurethane (Polymedica™). procedure was used for attachment of the biocide to the Polymedica™ polyurethane.

Proxel™ immobilised on Tecoflex™ and Polymedica™ polyurethane membranes were tested and compared with blank controls in a nutrient broth containing ∼$10^5$ colony forming units/ml. The membranes (immobilised Proxel™ and blanks) were cut into ∼1 cm² squares. First, the membranes were soaked in 70% ethanol (having first established they are immutable with the solvent) for 4 minutes and transferred to sterile pots and left in a laminar flow cabinet in a sterile environment with the lids off overnight. This ensured the membranes were sterile. Secondly, lengths of Ni/Cr wire and pieces of silicone rubber were autoclaved overnight in foil/cotton wool. Thirdly, 6 membrane squares were threaded onto a wire using the rubber spacers, this being carried out in duplicate. Finally, the assembled devices were placed in sterile glass tubes containing the broth and the bacteria (*Pseudomonas aeruginosa*) added. In addition to blank membranes, 2 tubes had the wire and spacers only and another 2 tubes had nothing (blank controls) as illustrated in FIG. 1.

100 μl aliquots were removed from the tubes at half hour intervals for the first 3 hours and subsequently hourly until 8 hours had elapsed, then 12 hours and 24 hours. These were diluted to $10^{-6}$ and plated onto nutrient agar; the viable bacteria were counted and the populations versus time calculated.

It was clear from visual observation during the experiment that the tubes containing the active material were clearer than the controls. This suggests that the bacterial population was lower when the biocide immobilised on polyurethane membrane was present since bacteria in water exhibit light scattering dependant on their concentration (above ∼$10^6$ cfu/ml).

EXAMPLE 2

Figure 2:
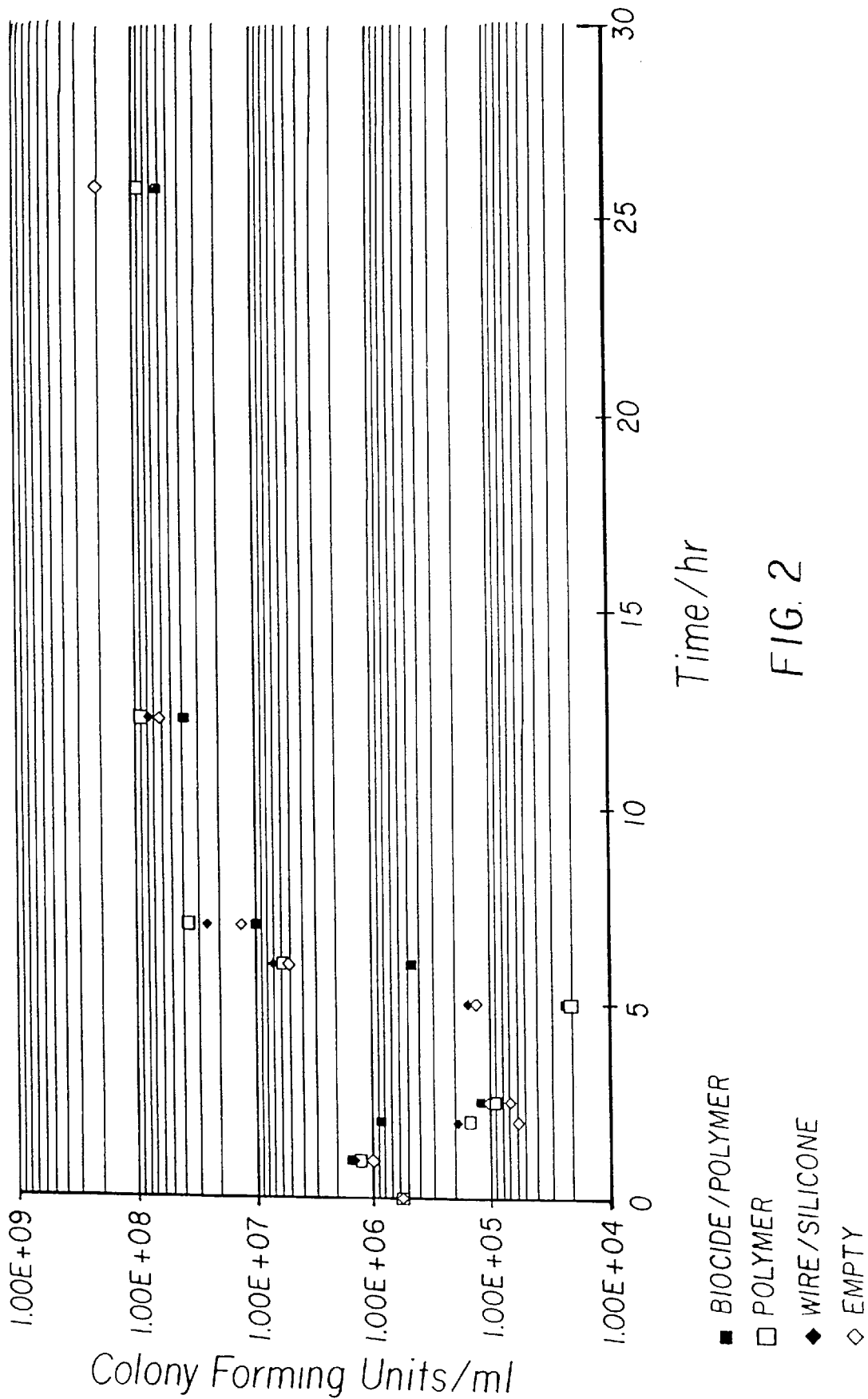
FIG. 2 is a graphical representation of results achieved using the invention in accordance with Example 2 described hereafter.

The experiment of Example 1 was repeated with 10 squares of Polymedica™ membranes on which Proxel™ had been immobilised. The same visual observations were made and the corresponding microbiological data are presented in FIG. 2. The bacterial population initially drops; this is the characteristic lag phase as the bacteria become accustomed to their new environment, before entering the exponential growth phase. The greatest difference between bacterial populations is seen at ∼6 hours where the immobilised biocide membrane clearly limits the growth of bacteria compared with the controls, before the stationary phased is reached (when there is no further increase in the number of bacteria). UV, HPLC and MS analysis of the broth solutions after the experiments suggested that the biocide remained attached to the support whilst in a simple aqueous medium, but on contact with the bacteria there seems to be some enzyme mediated cleavage, supplying biocide "on demand". However, no free biocide was detected by mass spectrometry in the filtered broth from tubes containing immobilised biocide resultant from this experiment.

The microbiological data shows that the immobilised biocide membrane can control or reduce the growth of bacteria in aqueous media.

We claim:

1. A method for inhibiting bacterial growth in wash water for a photoprocessing system comprising contacting the wash water of a photoprocessing system with a biocidal material comprising an organic biocide immobilized on a water-insoluble polymeric support in the form of a sheet, fiber or particle wherein the biocide is covalently bound to the support by a hydrolytically stable covalent linkage.

2. A method according to claim 1 wherein the biocide is an isothiazolinone.

3. A method according to claim 1 wherein the polymer support is a polyurethane, polyamide or a polyurea.

* * * * *